United States Patent [19]

Papas et al.

[11] Patent Number: 5,674,705

[45] Date of Patent: Oct. 7, 1997

[54] PRODUCTIVE OF HUMAN T-CELL LEUKEMIA (LYMPHOTROPIC) RETROVIRUS (HTLV-1) ENVELOPE PROTEIN FRAGMENTS IN BACTERIA AND USE IN SEROEPIDEMIOLOGICAL STUDIES

[75] Inventors: Takis S. Papas, Potomac; Kenneth Samuel, Hyattsville; James A. Lautenberger, Middletown; Flossie Wong-Staal, Pontomac, all of Md.

[73] Assignee: The United States of America as represented by the Department of Health and Human Services, Washington, D.C.

[21] Appl. No.: 194,818

[22] Filed: Feb. 14, 1994

Related U.S. Application Data

[63] Continuation of Ser. No. 979,343, Nov. 20, 1992, abandoned, which is a continuation of Ser. No. 126,007, Nov. 27, 1987, abandoned, which is a continuation-in-part of Ser. No. 664,972, Oct. 26, 1984, abandoned.

[51] Int. Cl.$^6$ .................... C12P 21/06; C12Q 1/70; G01N 33/53; C07K 1/00
[52] U.S. Cl. .................... 435/69.1; 435/5; 435/7.1; 435/252.33; 435/69.7; 435/69.3; 435/235.1; 530/350
[58] Field of Search .................... 530/350; 435/7.1, 435/5, 68, 172.3, 235.1, 69.3, 69.7, 69.1, 252.33, 320.1

[56] References Cited

U.S. PATENT DOCUMENTS

| | | | |
|---|---|---|---|
| 4,359,535 | 11/1982 | Piecznik | 435/172.3 |
| 4,406,885 | 9/1983 | Pinter | 424/89 |
| 4,520,113 | 5/1985 | Gallo | 436/504 |
| 4,525,300 | 6/1985 | Yoshida | 530/327 |
| 4,572,800 | 2/1986 | Shimuzu | 424/85 |
| 4,588,681 | 5/1986 | Sawada | 435/5 |

FOREIGN PATENT DOCUMENTS

| | | | |
|---|---|---|---|
| 041 767 | 12/1981 | European Pat. Off. | C12N 15/00 |
| 105 465 | 4/1984 | European Pat. Off. | C12P 21/00 |

OTHER PUBLICATIONS

Seiki, et al., 1983 "Human adult T-cell leukemia virus . . ." PNAS 80:3618-3622.
Maniatis, T et al., 1982 *Molecular Cloning*, Cold Spring Harbor Laboratory (Chapters 1, 10-12).
Sodroski, et al, 1984, "Sequence of the envelope glycoprotein . . ." Science 225:421-424.
Lautenberger, et al, 1983, "High-level expression in *Escherichia coli* . . ." Gene 23:75-84.
Arya, et al, 1984, "Homology of Genome of AIDS-Associated . . ." Science 225:927-930.
Schüpbach, et al, 1984, "Serological Analysis of a . . ." Science 224:503-505.
Sarngadharan, et al, 1984, "Antibodies reactive with . . ." Science 224:506-508.

R. Sodroski, et al., "Sequence of the Envelope Glycoprotein Gene of Type II Hyman T Lymphotropic Virus" Science 225: 421–424 (27 Jul. 1984).
H. Oppenheim, A. B., et al., "Regulation of Bacteriophage λ int Gene Expression", J. Molecular Biol. 158: 327–346 (1982).
I. Manzari, V., et al., "Human T-Cell Leukemia–Lymphoma Virus (HTLV): Cloning of an Integrated Defective Provirus and Flanking Cellular Sequences", PNAS 80:1574–1578 (Mar. 1983).
J. Schneider, J., et al., "Sera from Adult T-Cell Leukemia Patients React with Envelope and Core Polypeptides of Adult T-Cell Leukemia Virus", Virology, 132(1)1-11 (1984) cited in CA100(13):101335b.
K. Yoshida, M., et al. EP 113 078, published 11 Jul. 1984 cited in CA 101(19)164751a.
L. Hattori, et al., "Identification of gag and env Gene Protein Products of Human T-Cell Leukemia Virus (HTLV)", Virology, 136(2):338–347 (1987) cited in CA 101(25):223639v.
M. Kiyokawa, T., et al., "Envelope Proteins of Human T-Cell Leukemia Virus: Expression in *Escherichia coli* and its Application to Studies of env Gene Functions", PNAS 81(19):6202–6206 (19 Oct. 1984) cited in CA 101(25):223782m.
N. Seiki, M., et al., "Human Adult T-Cell Leukemia Virus: Molecular Cloning of the Provirus DNA and the Unique Terminal Structure", PNAS 79:6899–6902 (Nov. 1982).
O. Clapham, P., et al., "Pseudotypes of Human T-Cell Leukemia Virus Types 1 and 2: Neutralization by Patients' Sera", PNAS 81:2886–2889 (May 1984).
P. Essex, M. et al., "Antibodies to Human T-Cell Leukemia Virus Membrane Antigens (HTLVMA) in Hemophiliacs", Science 221:1061–1064 (Sep. 1983).
Q. Lautenberger, J. et al., Gene Anal. Techniques, 1:63–66 (1984).
R. Lautenberger, J., et al., Gene, 23:75–84 (1983).
S. Lautenberger, J. et al., Science, 221: 858–860 (1983).
T. Lautenberger, J. et al., Gene Amplification and Analysis, Vol. 3. "Expression of Cloned Genes in Prokaryotic and Eukaryotic Cells", Papas, et al. (eds)., Elsevier, pp. 147–174 (1983).
U. Seiki, M., et al., "Human Adult T-Cell Leukemia Virus: Complete Nucleoide Sequence of the Provirus Genome Integrated in Leukemia Cell DNA", PNAS 80: 3618–3622 (Jun. 1983).
V. Maniatis, T., et al., "Molecular Cloning" Cold Spring Harbor Laboratory, Chapters 1, 10-12 (1982).

(List continued on next page.)

*Primary Examiner*—Lynette F. Smith
*Attorney, Agent, or Firm*—Morgan & Finnegan, L.L.P.

[57] ABSTRACT

Antigenic proteins may be expressed in bacteria by use of vectors having inserted therein DNA fragments from an envelope gene. The DNA fragments employed in the example are coding sequences found in the HTLV-I envelope gene. The bacteria used was *E. coli*. The antigenic proteins are useful in identifying antibodies to the organisms from which the DNA fragments were originally obtained.

28 Claims, 3 Drawing Sheets

OTHER PUBLICATIONS

W. Arya, S. et al., "Homology of Genome of AIDS–Associated Virus with Genomes of Human T–Cell Leukemia Viruses", Science 225: 927–930 (31 Aug. 1984).

X. Yoshida, M., et al., "Isolation and Characterization of Retrovirus from Cell Lines of Human Adult T–Cell Leukemia and Its Implication in the Disease", PNAS 79:2031–2035 (Mar. 1982).

Y. Voller, A., et al., "Enzyme Immunoassays in Diagnostic Medicine", Bull. World Health Organ. 53:55–65 (1976).

Z. Lee, T. H., et al., "Human T–Cell Leukemia Virus–Associated Membrane Antigens: Identity of the Major Antigens Recognized After Virus Infection", PNAS 81:3856–3860 (Jun. 1984).

AA. Weis, J. H., et al., "An immunologically active chimaeric protein containing herpes simplex virus type 1 glycoprotein D", Nature 302: 72–74 (3 Mar. 1983).

PRODUCTIVE OF HUMAN T-CELL LEUKEMIA (LYMPHOTROPIC) RETROVIRUS (HTLV-1) ENVELOPE PROTEIN FRAGMENTS IN BACTERIA AND USE IN SEROEPIDEMIOLOGICAL STUDIES

This application is a continuation of application U.S. Ser. No. 07/979,343, filed Nov. 20, 1992, abandoned, which is a continuation of U.S. Ser. No. 07/126,007, filed Nov. 27, 1987, abandoned, which is a continuation-in-part of U.S. Ser. No. 06/664,972, filed Oct. 26, 1984, abandoned.

BRIEF DESCRIPTION OF THE INVENTION

The synthesis of proteins having antigenic properties of viral envelope proteins in bacteria via recombinant DNA techniques provides many advantages over previous methods of production. The antigens may be produced more rapidly at reduced cost. Furthermore, the antigens produced by the recombinant DNA techniques have a defined structure and are not subject to variation arising from mutation of the virus since the structure of the protein is defined by the input DNA.

While the antigens produced according to the inventive method may differ in secondary structure from proteins or protein fragments that are produced in the virus, the synthetically produced structures were recognized by antibodies that are produced in response to native viral protein. The proteins of the invention are useful as diagnostic tools and, when used as immunogens, will elicit production of antibodies which are reactive with the native virus.

The method of the invention was applied using two DNA fragments from human T-cell leukemia virus subgroup I (HTLV-I) envelope gene. The fragments were inserted into pJLA16 plasmids using polynucleotide linkers. These plasmids containing either of the DNA fragments were introduced into E. coli. The MZ1 strain of E. coli which contains a temperature-sensitive repressor was used as a preferred bacteria. The protein-containing fractions obtained from a lysate of the induced MZ1 cells were recognized by antibodies in sera from HTLV-I infected patients.

BACKGROUND OF THE INVENTION

Antibodies that react with HTLV-I proteins have been found in the sera of adult T-cell leukemia lymphoma (ATL) patients. These antibodies recognize both the gag core antigens and the envelope proteins of the virus. Viral core proteins were readily purified, sequenced, and extensively used in immunoassays; however, progress with the more important viral envelope proteins was slower. A limiting factor, therefore, in the studies of the immune response to these viruses has been the difficulty in isolating the viral envelope proteins in pure form and in quantity.

The proviral DNA of HTLV-I has been cloned [Seiki et al., Proc. Natl. Acad. Sci. USA, 79:6899 (1982) and Manzari et al., Proc. Natl. Acad. Sci. USA, 80:1574 (1983)] and sequenced [Seiki et al., Proc. Natl. Acad. Sci. USA, 80: 3618 (1983)]. The HTLV-I envelope is expressed by placing it into the pJLA16 derivative [Lautenberger et al., Gene Anal. Techniques, 1:63–66 (1984)] of plasmid pJLA6 [Lautenberger et al., Gene, 23:75 (1983)]. This plasmid contains the 13 amino-terminal codons of the bacteriophage lambda cII gene placed under the transcriptional control of the well-regulated phage lambda $p_L$ promoter. This plasmid is known and has been successfully used to express sequences from myc, myb, and ras oncogenes [Lautenberger et al., Gene, 23:75 (1983) and Lautenberger et al., in Gene Amplification and Analysis, Volume 3, Expression of Cloned Genes in Prokaryotic and Eukaryotic Cells, Papas et al (eds), Elsevier, New York/Amsterdam, pp. 147–174 (1983)].

DETAILED DESCRIPTION OF THE INVENTION

Figure 1:
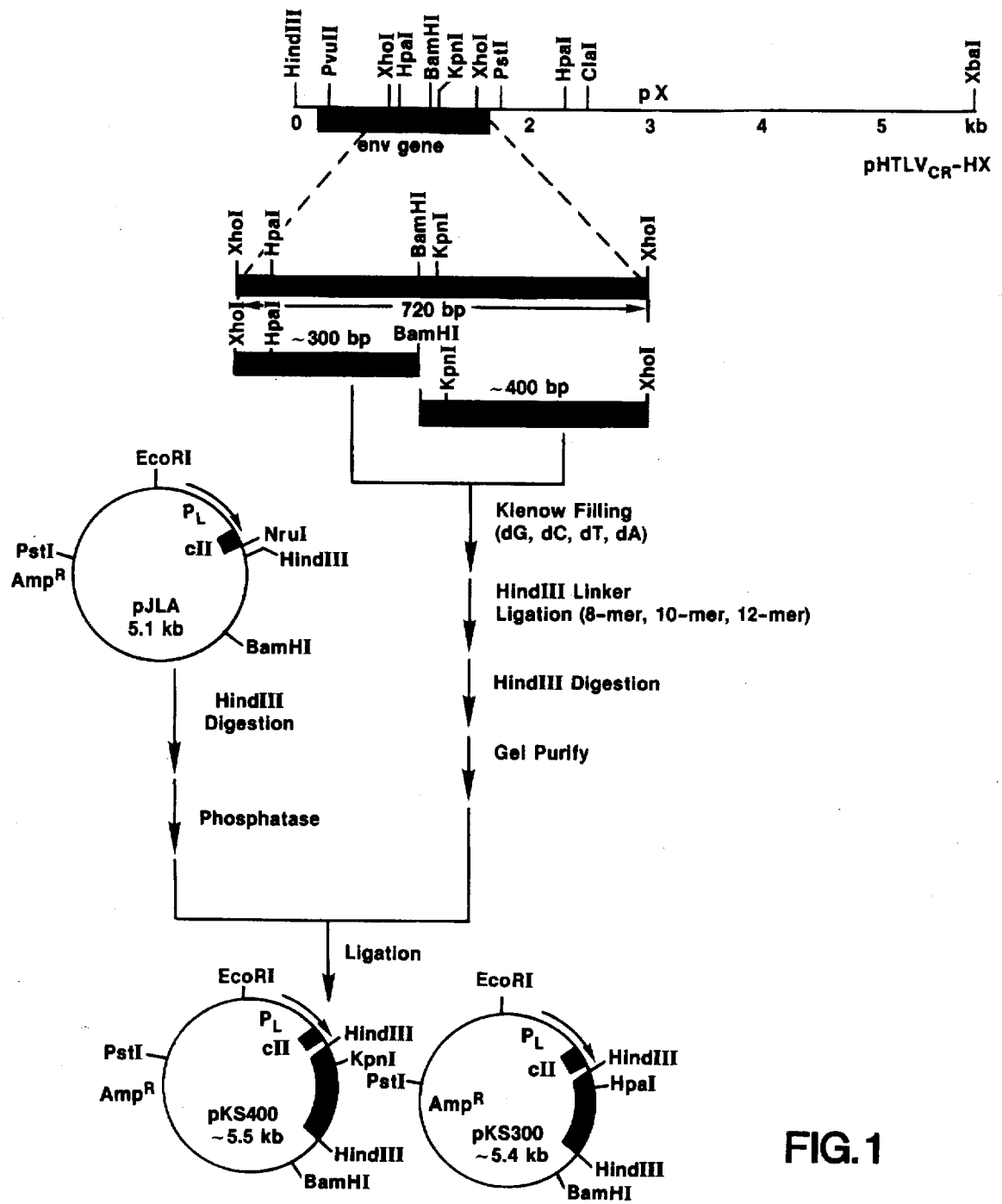
FIG. 1: Individual fragments of the HTLV envelope gene inserted into plasmid vector pJLA by the use of polynucleotide linkers.

Initial attempts to express the entire HTLV-I envelope were unsuccessful, possibly because this protein can interact with the bacterial cell membrane in such a way as to be toxic to the cell. Therefore, individual fragments coding for specific regions of the envelope were inserted into pJLA6 by use of poly-nucleotide linkers (FIG. 1).

The HTLV-I env gene codes for a glycoprotein (gp61) of molecular weight 61,000 that is cleaved into the molecular weight 46,000 exterior glycoprotein (gp46) and the molecular weight 21,000 trans membrane protein (gp21E). The precise site of proteolytic cleavage has been determined by locating radiolabeled valine residues with respect to the amino terminal end of gp21. The cleavage of the env gene precursor is adjacent to the residues Arg—Arg that also occur next to the proteolytic cleavage sites in the bovine leukemia virus (BLV) and mouse mammary tumor virus (MMTV) env precursor. Since the BamHI site that separates the inserted fragments is close to the region coding for proteolytic cleavage site that separates gp46 from p21E, the protein from pKS300 contains sequences corresponding to the carboxy-terminal portion of gp46 and the protein from pKS400 predominantly consists of sequences from p21E. Based on DNA sequence data of the envelope gene fragments utilized in the example, the calculated molecular sizes of the pKS300 and pKS400 proteins are 12.84 Kd and 15.88 Kd, respectively. These sizes include the 1.56 Kd coding sequence contributed by the amino terminal codons of the lambda cII gene. The observed molecular weights of both proteins on SDS-polyacrylamide gels are consistent with those calculated for a 321 base pair (pKS300 insert) and 397 base pair (pKS400 insert) coding sequences.

EXAMPLE 1

Construction of plasmids pKS300, now ATCC number 39902 and pKS400, now ATCC number 39903. Plasmid pHTLV-I HX-CR was obtained by subcloning the 5.7 kb Hind III-XbaI fragment of lambda CR1 [Manzari et al., Proc. Natl. Acad. Sci. USA, 79:6899 (1982)] that contained envelope, pX, and LTR sequences. Lambda CR1 contained integrated HTLV-I proviral DNA from mycosis fungoides patient CR. pHTLV-I HX-CR DNA was digested. XhoI and BamHI and the 300 bp and 400 bp fragments containing the env sequences were isolated from an agarose gel. The termini of these fragments were converted to blunt ends by the action of Klenow fragment *E. coli* DNA polymerase I and Hind III linkers were attached. Excess linkers were removed by digestion with Hind III and reisolation of the fragments from agarose gels. The pJLA16 [Lautenberger et al., *Gene Anal. Techniques*, 1:63–66 (1984)] vector DNA was cleaved with Hind III and the ends were dephosphorylated by the action of calf intestinal phosphatase. The dephosphorylated vector DNA was ligated to the fragment DNAs and introduced into DC646 cells by transformation using ampicillin selection. Plasmids containing inserts were identified by hybridization of colonies transferred to nitrocellulose with radiolabelled fragment produced by nick-translation of fragment DNA using [alpha-$^{32}$P]dCTP. For protein expression experiments, the plasmids were transferred into a prokaryote host such as by transferring into *E. coli* (strain MZ1) provided by M. Zuber and D. Court.

Figure 2:
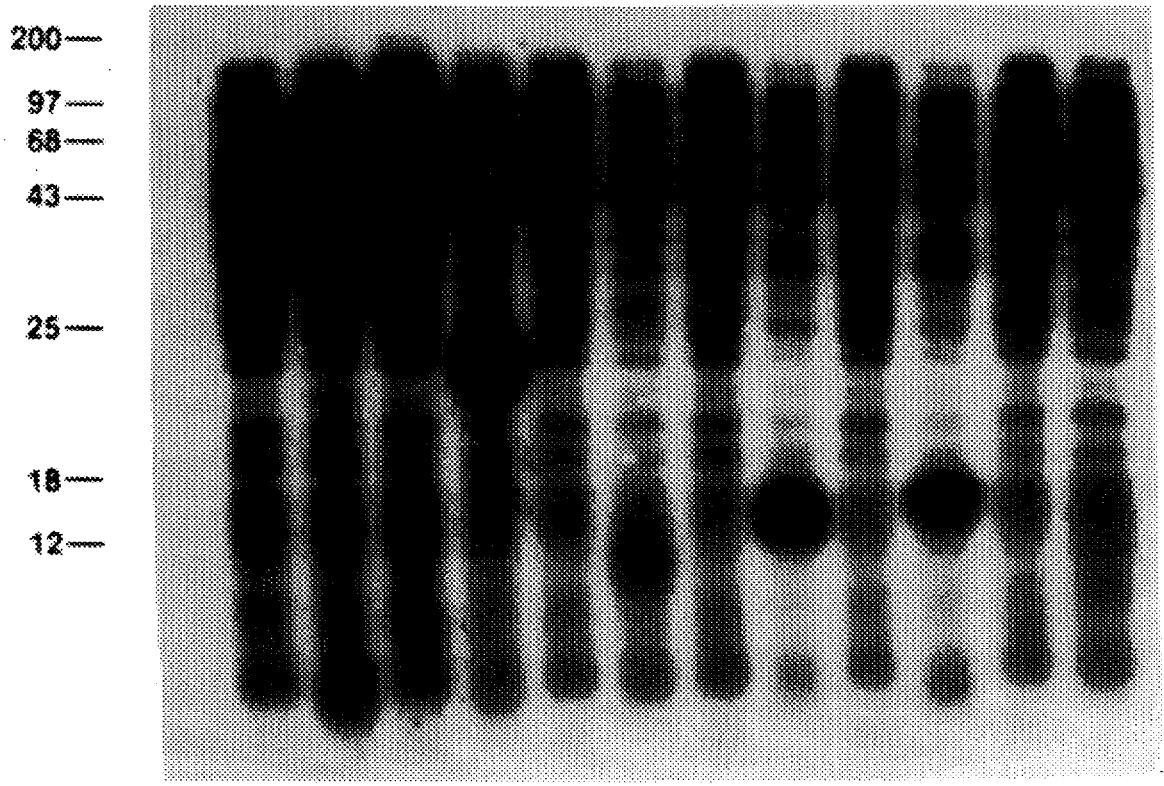
FIG. 2: Uninduced (U) and induced (I) E. coli cell extracts of expression plasmid vectors in gels stained for total protein.

The MZ1 strain contains a partial lambda prophage bearing the mutant cI857 temperature-sensitive repressor. At 32° C. the repressor is active and $p_L$ promoter on the plasmid is repressed. At 42° C. the repressor is inactive and the $p_L$ promoter is induced, allowing high level expression of genes under its transcriptional control. When lysogens carrying either of the two plasmids containing different portions of the HTLV-I envelope gene (cf. ante) were grown at 32° C. and induced by shifting the temperature to 42° C., prominent bands were observed that were not found in uninduced cells or in induced cells containing the pJL6 vector alone (FIG. 2).

EXAMPLE 2

Expression of the HTLV-I envelope gene in *E. coli*.

(a) Radiolabeling of bacterial cell proteins. *E. coli* MZ1 cells were grown at 32° C., induced by shifting the temperature to 41° C., labeled with [$^{35}$S]-cysteine and lysed. Proteins were resolved by sodium dodecyl sulfate-polyacrylamide gel electrophoresis (SDS-PAGE) and visualized by autoradiography.

(b) Uninduced (U) and induced (I) cell extracts of expression plasmid vectors were observed in gels stained for total protein. See FIG. 2 showing Lane 1, pJL6 vector without insert; Lane 2, pJLcII ras; Lane 3, pKS300; Lane 4, pKS400.1; Lane 5, pKS400.2; Lane 6, 400 bp fragment in wrong orientation.

Figure 3:
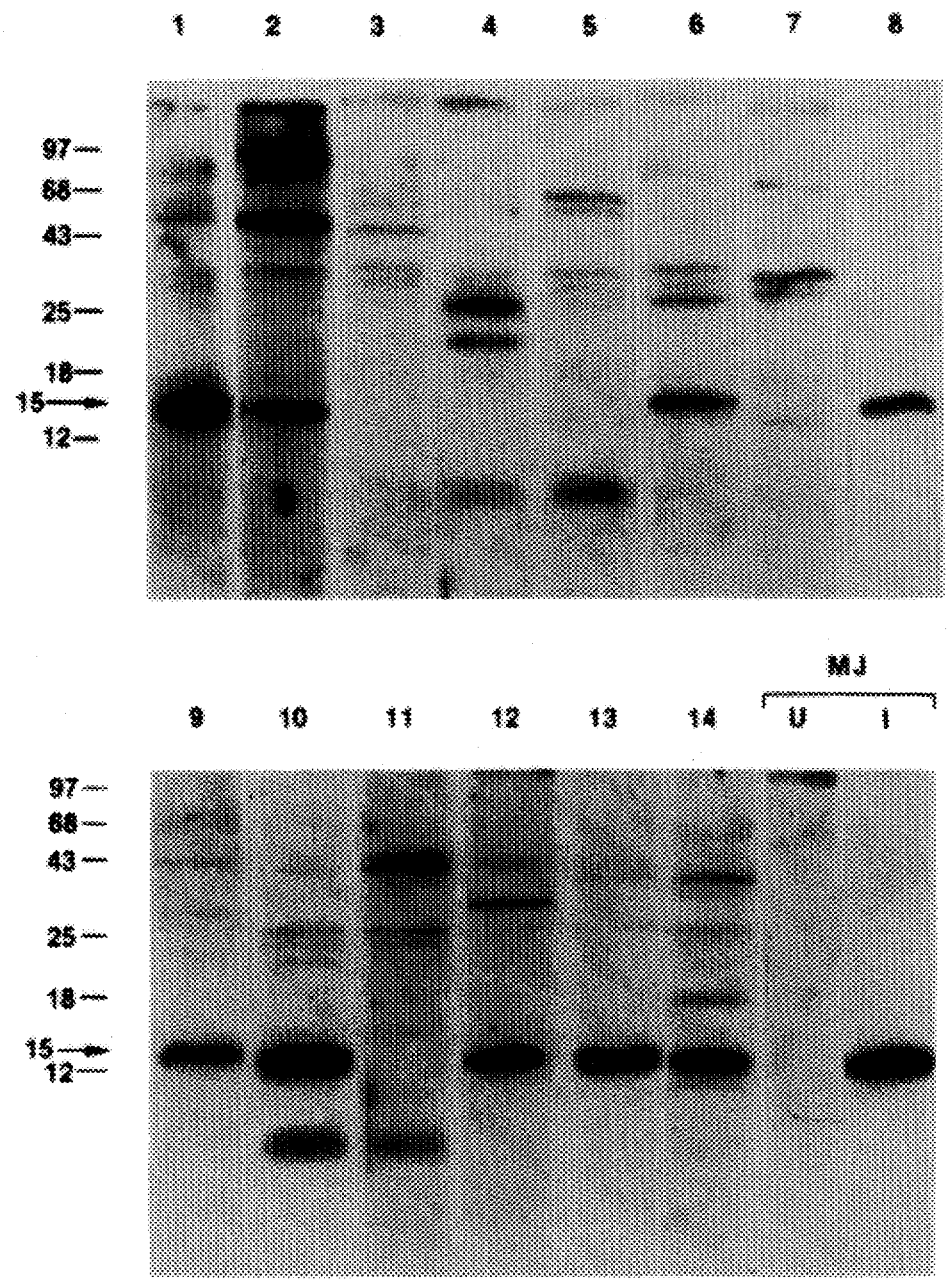
FIG. 3: Western blot of HTLV envelope products produced in bacteria expressing the pKS400-encoded polypeptide. Prominant 15 kd band indicates immunoreactivity of the bacterial envelope product with sera from HTLV infected patients. Sera from individuals 1–8 as described in Example 3 are shown in lanes 1–8 of the upper panel. Sera from individuals 9–14 as described Example 3 are shown in lanes 9–14 of the lower panel. Lane 15 and 16 of the lower panel show uninduced and induced extracts reacted with serum from patient MJ as described in Example 3.

In order to see if such antibodies can recognize a bacterially synthesized envelope product, a lysate of induced MZ1[pKS400] cells containing this protein was fractionated by SDS-polyacrylamide gel electrophoresis and transferred to nitrocellulose sheets by electrophoretic (Western) blotting. Strips containing the transferred proteins were reacted with diluted human serum and antigen-antibody complexes formed were detected by incubation of the strips with $^{125}$I-labeled *Staphlococcus aureus* protein A followed by autoradiography. As shown in FIG. 3, prominent bands corresponding to reaction of antibody to the 15 Kd bacterial envelope product could readily be observed when the serum used was from patients with HTLV-I associated ATL or from HTLV-I antigen (+) individuals. No such reaction bands were observed with sera from healthy control individuals. This procedure was used to screen a group of 28 coded sera. Antibodies that recognized the bacterially synthesized HTLV-I envelope protein sequences were found in all sera that had been shown to have anti-HTLV-I antibodies by ELISA assay using disrupted virions as antigen (Table 1). Thus, a method is formulated for serologically testing for the presence in human sera of antibodies directed against HTLV-I or HTLV-II. None of the normal control sera were found to have reacting antibodies. Antibodies from a patient (Mo) with a hairy cell leukemia, whose disease is associated with HTLV-II, strongly reacted to the protein coded for in pKS400 indicating that there is a high degree of relatedness between the p21E region of HTLV-I and HTLV-II.

EXAMPLE 3

Recognition of Bacterial Synthesized HTLV-I Envelope Protein by Antibodies in Human Serum MZ1 [pKS400] cells were grown at 32° C., induced at 42° C., and lysed in the presence of 1% SDS-0.1% beta-mercaptoethanol. Protein in the extracts were resolved by SDS-PAGE and electrophoretically transferred to nitrocellulose paper by the "Western blot" procedure. After transfer, filters were air dried and soaked in TBS-NDM (50 mM Tris-HCl, pH 7.5, 500 mM NaCl, 3% Nonfat Dry Milk). The filters were incubated overnight at room temperature in TBS-NDM plus 1/77 volume human serum as indicated below. Filters were then washed with TBS-NDM for 30 min and then incubated with $10^5$ cpm [$^{125}$I]-protein (NEN). The filter was then washed with TBS-NDM and finally with TBS. The filters were air dried and protein bands reacting with antibody were visualized by autoradiography (see FIG. 3). The sera used were: (1) American ATL patient; (2) T-cell hairy cell leukemia patient Mo (Ref. 4); (3) Healthy normal

TABLE 1

Presence of Antibodies Recognizing Bacterially Synthesized HTLV-I Envelope in Human Sera

| Status | HTLV-I or HTLV-II +/− (by ELISA) | Number Tested | Number Positive |
| --- | --- | --- | --- |
| Clinically normal heterosexual | + | 2 | 2/2 |
|  | − | 8 | 0/8 |
| Clinically normal homosexual | − | 5 | 0/5 |
| AIDS patients | + | 2 | 2/2 |
|  | − | 2 | 0/2 |
| ATL patients | + | 5 | 5/5 |
| Mycosis fungoides patient | + | 1 | 1/1 |
| Hairy cell leukemia patient Mo (HTLV-I + patient) | + | 1 | 1/1 |
| Lymphadenopathy syndrome patients | − | 2 | 0/2 |

(4) Healthy normal; (5) Healthy normal; (6) Healthy relative of ATL patient; (7) Healthy normal; (8) Japanese ATL patient; (9) AIDS patients found to be HTLV-II (+) by ELISA (disrupted virus antigen); (10) AIDS patient found to be HTLV-I (+) by ELISA (disrupted virus antigen); (11) Healthy normal; (12) American ATL patient; (13) Mycosis fungoides patient; (14) Healthy normal found to be HTLV-I (+) by ELISA (disrupted virus antigen). Uninduced and induced extracts pKS400.2 reacted with patients MJ serum (HTLV-I positive by ELISA).

Since the bacterially synthesized HTLV-I env protein was recognized by antibodies present in sera from AIDS patients, it was also of interest to show that this assay can be utilized to screen for a more distantly related subgroup, namely, HTLV-III (known now as HIV, causative agent of AIDS). Therefore, a number of sera samples of AIDS patients, some of which were also sero-positive for HTLV-I, were examined.

The sera from all positive AIDS patients which reacted with HTLV-I in ELISA contained antibodies that recognized the bacterial synthesized HTLV-I env protein. None of the sera from AIDS patients that were HTLV-I negative contained antibodies that reacted with the bacterial protein. Since antibodies that react with HTLV-III proteins can be found in the serum of greater than 90% of AIDS patients, this result indicates that there is little or no cross reaction between the carboxy-terminal portion of the envelope proteins of HTLV-I and HTLV-III.

pKS300 and pKS400 have been deposited with the American Type Cell Culture Collection (ATCC) at 12301 Parklawn Drive, Rockville, Md. 20852. pKS300 has the ATCC designation of 39902, and pKS400 has the ATCC designation of 39903.

What is claimed is:

1. A method of producing immunoreactive HTLV-I envelope polypeptide fragments, comprising the steps of:
   (a) isolating the envelope gene of HTLV-I
   (b) cleaving the HTLV-I envelope gene with restriction enzymes XhoI and BamHI to generate at least two envelope gene fragments: one gene fragment of about 300 base pairs that encodes an immunoreactive polypeptide containing amino acid sequences from the carboxy terminal portion of the external envelope glycoprotein gp46 and another gene fragment of about 400 base pairs that encodes an immunoreactive polypeptide containing amino acid sequences of the envelope transmembrane polypeptide p21E;
   (c) attaching polynucleotide linkers to the gene fragments produced in step (b);
   (d) inserting the envelope gene fragments produced in step (c) into expression vectors;
   (e) introducing the vectors produced in step (d) into prokaryotic host cells; and
   (f) isolating the expressed immunoreactive HTLV-I envelope exterior glycoprotein and transmembrane polypeptide fragments from lysates of the host cells.

2. The method according to claim 1, wherein the host cell is E. coli bearing a temperature-sensitive repressor.

3. The method according to claim 2, wherein the E. coli is strain MZ1.

4. The method according to claim 1, wherein the vector of step (d) is plasmid vector pJLA16.

5. The method according to claim 4, wherein the plasmid insert is pKS400 having ATCC Accession No. 39903.

6. The method according to claim 4, wherein the plasmid insert is pKS300 having ATCC Accession No. 39902.

7. A method of producing an immunoreactive HTLV-I envelope transmembrane polypeptide fragment comprising:
   (a) isolating the envelope gene of HTLV-I;
   (b) cleaving the HTLV-I envelope gene with restriction enzymes XhoI and BamHI to generate one gene fragment of about 300 base pairs encoding an immunoreactive exterior envelope glycoprotein polypeptide containing amino acids from the carboxy terminal portion of the gp46 envelope polypeptide and one gene fragment of about 400 base pairs encoding an immunoreactive envelope transmembrane polypeptide containing amino acids of the p21E envelope polypeptide;
   (c) inserting said cleaved gene fragment encoding said p21E transmembrane polypeptide fragment into an expression vector so that said gene fragment encoding said transmembrane polypeptide fragment is operably linked to a promoter present in said expression vector;
   (d) introducing said expression vector resulting from step (c) into a procaryotic host cell under conditions such that said envelope gene fragment encoding said p21E envelope transmembrane polypeptide fragment is expressed and produces said envelope transmembrane polypeptide; and
   (e) isolating said expressed and produced transmembrane polypeptide fragment.

8. The method according to claim 7, wherein said transmembrane polypeptide is encoded by the pKS400 plasmid insert having ATCC Accession No. 39903.

9. The method according to claim 7, wherein said host cell is E. coli bearing a temperature-sensitive repressor.

10. A method of producing an immunoreactive HTLV-I envelope polypeptide fragment of HTLV exterior glycoprotein comprising:
    (a) isolating the envelope gene of HTLV-I;
    (b) cleaving the HTLV-I envelope gene with restriction enzyme XhoI and BamHI to generate one gene fragment of about 300 base pairs encoding an immunoreactive exterior envelope glycoprotein polypeptide containing amino acids from the carboxy terminal portion of the gp46 envelope polypeptide and one gene fragment of about 400 base pairs encoding an immunoreactive envelope transmembrane polypeptide containing amino acids of the p21E envelope polypeptide;
    (c) inserting said cleaved gene fragment encoding said exterior glycoprotein polypeptide fragment into an expression vector so that said gene fragment encoding said immunoreactive exterior glycoprotein polypeptide fragment is operably linked to a promoter present in said expression vector;
    (d) introducing said expression vector resulting from step (c) into a prokaryotic host cell under conditions such that said envelope gene fragment encoding said exterior glycoprotein polypeptide fragment is expressed and produces said exterior envelope glycoprotein polypeptide fragment; and
    (e) isolating said expressed and produced exterior glycoprotein polypeptide fragment.

11. The method according to claim 10, wherein said exterior glycoprotein polypeptide fragment is encoded by the pKS300 plasmid insert having ATCC Accession No. 39902.

12. The method according to claim 7 or claim 10, wherein said host cell is E. coli bearing a temperature-sensitive repressor.

13. The method according to claim 12, wherein the E. coli host cell is E. coli strain MZ1.

14. The method according to claim 1 or claim 7, wherein the isolated envelope transmembrane polypeptide fragment has a calculated molecular weight of about 15.88 kilodaltons and migrates on SDS-polyacrylamide gels at a position corresponding to a 15–16 kilodalton molecular weight standard.

15. The method according to claim 1 or claim 10, wherein the isolated envelope exterior glycoprotein polypeptide fragment has a calculated molecular weight of about 12.84 kilodaltons and migrates on SDS-polyacrylamide gels at a position corresponding to a 12–13 kilodalton molecular weight standard.

16. The method according to claim 9, wherein the E. coli host cell is E. coli strain MZ1.

17. The method according to claim 6, or claim 11, wherein the pKS300 insert having ATCC Accession No. 39902 encodes an envelope polypeptide fragment having a calculated molecular weight of about 12.84 kilodaltons and migrating on SDS-polyacrylamide gels at a position corresponding to a 12–13 kilodalton molecular weight standard.

18. The method according to claim 5, or claim 8, wherein the pKS400 insert having ATCC Accession No. 39903 encodes an envelope polypeptide fragment having a calculated molecular weight of about 15.88 kilodaltons and migrating on SDS-polyacrylamide gels at a position corresponding to a 15–16 kilodalton molecular weight standard.

19. The method according to any one of claims 1, 7, or 10, further comprising the step of reacting said isolated and expressed envelope polypeptide fragment with sera and detecting immunoreactive anti-HTLV-I antibodies.

20. A method of producing immunoreactive HTLV-I envelope polypeptide fragments, comprising the steps of:
 (a) isolating the envelope gene of HTLV-I;
 (b) cleaving the HTLV-I envelope gene with restriction enzymes XhoI and BamHI to generate at least two envelope gene fragments: one gene fragment of about 300 base pairs that encodes an immunoreactive polypeptide containing amino acid sequences from the carboxy terminal portion of the external envelope glycoprotein gp46 and another gene fragment of about 400 base pairs that encodes an immunoreactive polypeptide containing amino acid sequences of the envelope transmembrane polypeptide p21E;
 (c) attaching polynucleotide linkers to the gene fragments generated in step (b);
 (d) inserting the envelope gene fragments produced in step (c) into expression vectors, said expression vectors resulting in the plasmids pKS300 having ATCC Accession No. 39902 and pKS400 having ATCC Accession No. 39903; and
 (e) introducing the vectors produced in step (d) into prokaryotic host cells.

21. The method according to claim 20, further comprising the step of:
 (f) isolating said expressed immunoreactive envelope exterior glycoprotein and transmembrane polypeptide fragments from lysates of the host cells.

22. A method of producing an immunoreactive HTLV-I envelope transmembrane polypeptide fragment comprising:
 (a) isolating the envelope gene of HTLV-I;
 (b) cleaving the HTLV-I envelope gene with restriction enzymes XhoI and BamHI to generate at least two gene fragments from said envelope gene: one gene fragment of about 300 base pairs encoding an immunoreactive exterior envelope glycoprotein polypeptide containing amino acids from the carboxy terminal portion of the gp46 envelope polypeptide and one gene fragment of about 400 base pairs encoding an immunoreactive envelope transmembrane polypeptide containing amino acids of the p21E envelope polypeptide;
 (c) inserting said gene fragment encoding said p21E transmembrane polypeptide fragment into an expression vector so that said gene fragment encoding said transmembrane polypeptide fragment is operably linked to a promotor present in said expression vector; wherein said vector is plasmid pKS400 having ATCC Accession No. 39903; and
 (d) introducing said expression vector resulting from step (c) into a prokaryotic host cell under conditions such that said envelope gene fragment encoding said envelope transmembrane polypeptide fragment is expressed and produces said envelope transmembrane polypeptide.

23. The method according to claim 22, further comprising the step of:
 (e) isolating said expressed and produced immunoreactive transmembrane polypeptide fragment.

24. A method of producing an immunoreactive HTLV-I envelope polypeptide fragment of HTLV-I exterior glycoprotein comprising:
 (a) isolating the envelope gene of HTLV-I;
 (b) cleaving the HTLV-I envelope gene with restriction enzymes XhoI and BamHI to generate one gene fragment of about 300 base pairs encoding an immunoreactive exterior envelope glycoprotein polypeptide containing amino acids from the carboxy terminal portion of the gp46envelope polypeptide and one gene fragment of about 400 base pairs encoding an immunoreactive envelope transmembrane polypeptide containing amino acids of the p21E envelope polypeptide;
 (c) inserting said cleaved gene fragment encoding said exterior glycoprotein polypeptide fragment into an expression vector so that said gene fragment encoding said exterior glycoprotein polypeptide fragment is operably linked to a promoter present in said expression vector; wherein said vector is plasmid pKS300 having ATCC Accession No. 39902; and
 (d) introducing said expression vector resulting from step (c) into a prokaryotic host cell under conditions such that said envelope gene fragment encoding said exterior glycoprotein polypeptide fragment is expressed and produces said exterior envelope glycoprotein polypeptide fragment.

25. The method according to claim 24, further comprising:
 (e) isolating said expressed and produced exterior glycoprotein polypeptide fragment.

26. A method of producing immunoreactive HTLV-I envelope polypeptide fragments, comprising the steps of:
 (a) isolating the envelope gene of HTLV-I;
 (b) cleaving the HTLV-I envelope gene to generate at least two envelope gene fragments: one gene fragment of about 300 base pairs that encodes an immunoreactive polypeptide containing amino acid sequences from the carboxy terminal portion of the external envelope glycoprotein gp46 and another gene fragment of about 400 base pairs that encodes an immunoreactive polypeptide containing amino acid sequences of the envelope transmembrane polypeptide p21E;
 (c) attaching polynucleotide linkers to the gene fragments generated in step (b);
 (d) inserting me envelope gene fragments produced in step (c) into expression vectors, said expression vectors resulting in the plasmids pKS300 having ATCC Accession No. 39902 and pKS400 having ATCC Accession No. 39903; and
 (e) introducing the vectors produced in step (d) into prokaryotic host cells.

27. The method according to claim 26, further comprising the step of:
 (f) isolating said expressed immunoreactive envelope exterior glycoprotein transmembrane polypeptide fragments from lysates of the host cells.

28. A composition of matter comprising the envelope polypeptide fragments produced according to the methods of claim 1, claim 7, or claim 10, bound to a solid support or with a carrier.

* * * * *